(12) United States Patent
Cuccinello

(10) Patent No.: US 11,375,910 B2
(45) Date of Patent: Jul. 5, 2022

(54) PULSE SENSING DEVICE

(71) Applicant: Joseph Cuccinello, Nutley, NJ (US)

(72) Inventor: Joseph Cuccinello, Nutley, NJ (US)

( * ) Notice: Subject to any disclaimer, the term of this patent is extended or adjusted under 35 U.S.C. 154(b) by 637 days.

(21) Appl. No.: 16/146,071

(22) Filed: Sep. 28, 2018

(65) Prior Publication Data

US 2019/0090765 A1   Mar. 28, 2019

Related U.S. Application Data

(60) Provisional application No. 62/564,751, filed on Sep. 28, 2017.

(51) Int. Cl.
| | | |
|---|---|---|
| *A61B 5/02* | (2006.01) | |
| *A61B 5/024* | (2006.01) | |
| *A61B 5/00* | (2006.01) | |
| *A61B 5/1455* | (2006.01) | |
| *A61B 17/132* | (2006.01) | |

(52) U.S. Cl.
CPC ...... *A61B 5/02427* (2013.01); *A61B 5/02416* (2013.01); *A61B 5/1455* (2013.01); *A61B 5/14552* (2013.01); *A61B 5/6832* (2013.01); *A61B 5/74* (2013.01); *A61B 17/132* (2013.01); *A61B 5/742* (2013.01); *A61B 17/1325* (2013.01); *A61B 2560/0214* (2013.01); *A61B 2560/04* (2013.01); *A61B 2560/0406* (2013.01); *A61B 2562/04* (2013.01); *A61B 2562/043* (2013.01)

(58) Field of Classification Search
None
See application file for complete search history.

(56) References Cited

U.S. PATENT DOCUMENTS

| | | |
|---|---|---|
| 5,919,133 A | 7/1999 | Taylor et al. |
| 6,572,636 B1 | 6/2003 | Hagen et al. |
| 7,418,284 B2 | 8/2008 | DeLonzor et al. |
| 7,569,018 B1 | 8/2009 | Geddes et al. |
| 8,273,053 B2 | 9/2012 | Saltzstein |
| 9,386,953 B2 | 7/2016 | Ai-Aii |
| 9,579,020 B2 | 2/2017 | Libbus et al. |
| 2006/0030781 A1 | 2/2006 | Shennib |
| 2014/0058469 A1 | 2/2014 | Owen et al. |
| 2014/0288381 A1 | 9/2014 | Faarbaek et al. |

FOREIGN PATENT DOCUMENTS

CA       2530414 C       1/2005

*Primary Examiner* — Marjan Fardanesh
(74) *Attorney, Agent, or Firm* — Gearhart Law LLC

(57) ABSTRACT

A pulse sensing device including main body with at least a pair of sensors, a power source, a power connector, at least one light source electrically coupled to the at least a pair of sensors and a divider configured to separate the power source from the power connector, a casing surrounding the main body, and, an adhesive layer located on a surface of the casing.

20 Claims, 3 Drawing Sheets

PULSE SENSING DEVICE

CLAIM OF PRIORITY

This application claims priority to U.S. Application 62/564,751 filed on Sep. 28, 2017, the contents of which are herein fully incorporated by reference in its entirety.

FIELD OF THE EMBODIMENTS

The field of the embodiments relate to a device and a method of using the device that allows a user to easily detect and measure the strength of a pulse on a person without having to apply the device to a precise region of a body while having the device be deformable and disposable.

BACKGROUND OF THE EMBODIMENTS

In life threatening and other emergency situations it is important to accurately check for a pulse. Personnel need to know when CPR has to be administered, and situations where amputation is possible the placement of a tourniquet is critical pulse detection plays a critical role. It is important to ensure that arterial blood flow is at a minimum, that tissue and vessels that are salvaged are not damaged and that as little as possible of a limb will be removed. Studies have suggested that trained medical personnel are able to identify a pulse accurately using manual methods only 55% of the time. The rates for non-trained personnel being able to identify a pulse manually are even lower. It is vital that medical personnel have access to a device that is able to quickly and accurately check for a pulse or lack thereof. Several attempts have previously been made at making pulse detection easy.

Examples of related art are described below:

U.S. Pat. No. 6,572,636 pertains to pulse sensing patch. The patch includes a visual indicator positioned to overlie a pulse sensor within a housing for displaying a visually recognizable pattern of the pulse. The method of using the pulse sensing patch preferably includes removing the pulse sensing patch from a sterile package, positioning the pulse sensing patch to overlie a user's skin, activating the pulse sensing patch by removing a lubricant cover positioned adjacent a lower surface of the medical pulse sensing patch, and visualizing a predetermined indication pattern representing the pulse. However, the structure of the patch still requires the patch to be initially placed at a specific pulse site, and slid around if a pulse is not detected initially.

U.S. App. 2014/0288381 pertains to a device to be attached to the body surface of a mammal that includes a microelectronic sensing system. The microelectronic system is for monitoring physiological or neurological conditions in the body. This device however is more invasive, uses electrocardiograms, and also requires precise placement by a trained professional.

None of the art described above addresses all of the issues that the present invention does. The present application provides a device that can be used by a lay person, and be placed anywhere on the body in order to identify the strength and quality of the pulse.

SUMMARY OF THE EMBODIMENTS

Embodiments of the present invention include a pulse sensing device that includes a main body comprising at least a pair of sensors, a power source, a power connector, at least one light source electrically coupled to the at least a pair of sensors and a divider configured to separate the power source from the power connector, a casing surrounding the main body, and, an adhesive layer located on a surface of the casing.

It is an object of the embodiments of the present invention that the sensors are photo sensors, comprise lasers, or oximetry sensors.

It is another object of the embodiments of the present invention that the casing is deformable, and is made of non-latex medical grade disposable foam, or PVA foam.

It is yet another object of the embodiments of the present invention that the light source is a light emitting diode.

It is yet another object of the embodiments of the present invention that the power source is a non-rechargeable battery.

It is yet another object of the embodiments of the present invention that the main body has a length of at least 80 millimeters and a width of at least 10 millimeters.

It is yet another object of the embodiments of the present invention that a ratio of the at least a pair of sensors to a length of the main body is at least 2 sensors to 10 millimeters.

It is yet another object of the embodiments of the present invention that the ratio of the at least a pair of sensors to the at least one light source is at least 2 to 1.

It is yet another object of the embodiments of the present invention that the divider includes a first section located inside the casing and a second section located outside the casing and is made of plastic.

It is yet another object of the embodiments of the present invention that the method of using the pulse sensing device, includes providing the pulse sensing device, having a user engage the power source, having the user contact the adhesive layer to a body part; and having the first light source or the second light source activate if a pulse is detected.

It is yet another object of the embodiments of the present invention that pulse detected is above 5 beats per minute or at least 25% of a normal sinus rhythm.

It is yet another object of the embodiments of the present invention that the method further includes providing a tourniquet, having the user apply the tourniquet to a body part at a first location with a first amount of force, having the user engage the power source, having the user contact the adhesive layer to the body part, having the first light source or the second light source activate if a pulse is detected, having the user apply the tourniquet with a second amount of force, wherein the second amount of force is greater than the first amount of force, and the light source being deactivated when a given threshold is reached.

DESCRIPTION OF THE PREFERRED EMBODIMENTS

Figure 1:
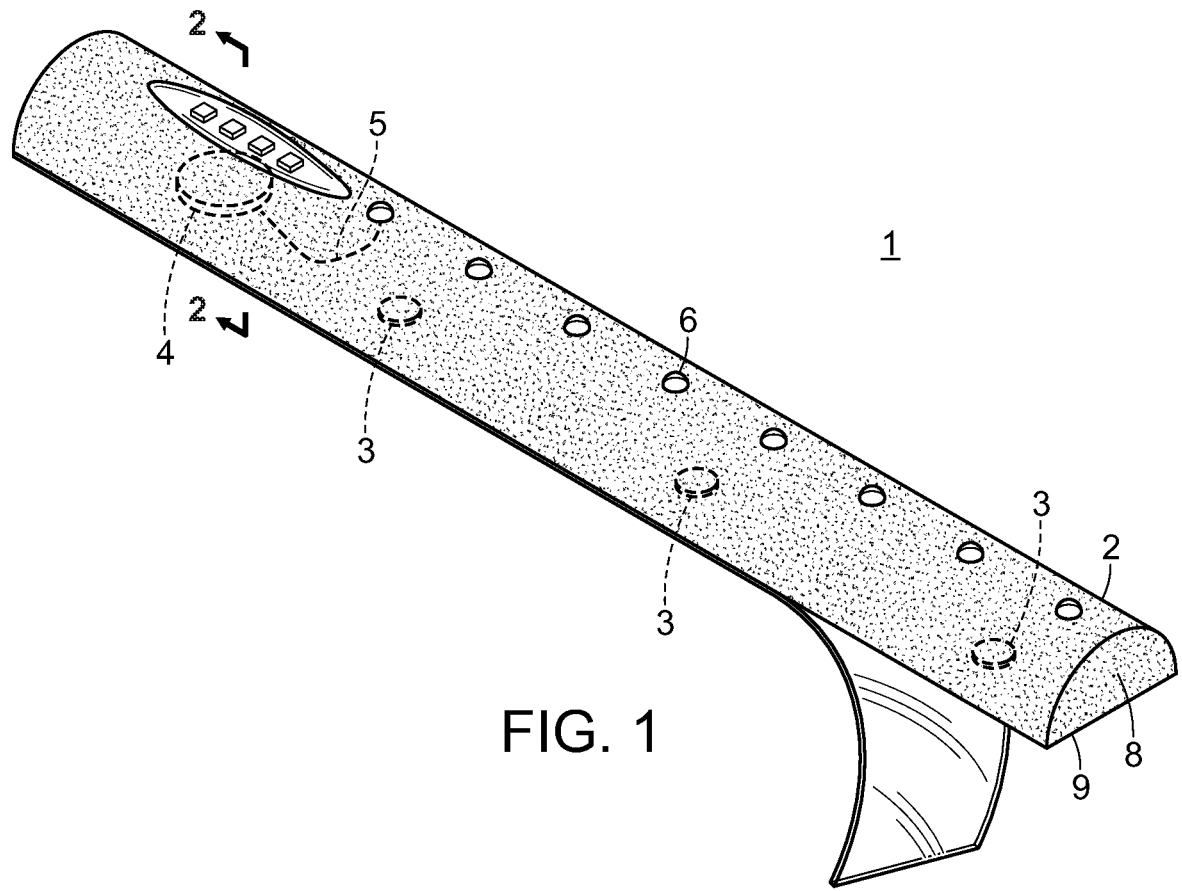
FIG. 1 shows a top perspective view of an embodiment of the invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

FIG. 1 displays a pulse sensing device. The device can include a main body 2 which includes at least a pair of sensors 3, a power source, a power connector 5, at least one light source 6 that can be electrically coupled to the pair of sensors. The main body 2 can also include a divider 7 that can separate the power source 4 from the power connector 5. The main body 2 can be surrounded by a casing 8. Further, an adhesive layer 9 can be placed on an outer surface of the casing 8. The adhesive layer 9, can help secure the device 1 in place and can also help detect the pulse by enhancing various aspects of the skin, such as conductance and heat transfer.

The casing 8 can be elongated in one or multiple directions such that it can be placed on a body part in various locations and orientations and still functions properly, detect a pulse, and determine if it is above a certain threshold. The casing 8 can have various shapes, it can be elongated, square, circular or any combination of shapes. The purpose of having multiple sensors 3 spaced out within the casing in one or multiple directions is that at least one of sensors 3 will sit atop or in very close proximity to an artery. In order to be reliable at detecting a pulse, a sensor 3 should be placed approximately about every 5 to 10 millimeters. The sensors 3 can be photo sensors, the sensors can include lasers and be laser based, or be oximetry sensors. The sensors 3 have to be capable of picking up a pulse during a low-flow state of CPR output, specifically at least at 25 percent of normal sinus rhythm.

The casing 8 serves several other purposes. The aforementioned components are arranged and secured within the casing 8. The casing 8, also provides a filtering and isolating qualities for the sensors 3. The sensors 3 have to be capable of detecting a pulse correctly without being affected by outside vibrations, which are typical in hectic emergency situations. The casing 8 can be made of non-latex medical grade disposable foam or PVA foam, essentially composed of Polyvinyl Alcohol and be deformable. A typical PVA sponge is hydrophilic and can hold up to 12 times its dry weight in water. In order to be medical grade, a foam must have been tested, passed and certified to comply with the ISO 10993 protocol and the raw material formulation of the foam may be registered with the FDA. Being easily disposable is another important benefit of this device. All similar devices are large, expensive, and cannot be disposed of easily.

As further seen in FIG. 1, the light source 6 can be a light emitting diode or a series of diodes capable of lighting up with a necessary color based on the condition of the pulse that is detected. For instance in one application, if a strong pulse, anything above approximately 30 beats per minute is detected, the diode can glow green, if a weak pulse, anything between approximately 5 and 30 beats per minute is detected the diode can glow a yellow color, and any pulse detected to be about 5 beats per minute or below, the diode can grow red or not light up at all. The color schemes and beat thresholds can be changed and interchanged in order to make the device more suitable for a particular application. The light sources 6, or diodes, can be placed adjacent to each sensor, or in a smaller frequency. The light sources can also be placed between each pair of sensors 3. Individual lights can be capable of lighting up, if any of the sensors connected to it, or to any of the other lights, detect a pulse. For instance, if a number of sensors 3 detect a very weak pulse or do not detect one at all, and one or a number of other sensors 3 detect a strong pulse over 30 beats per minute, the lights could be programmed to all light up green or all light up red, depending on the requirements of the application.

The preferred the power source 4 for the device is a non-rechargeable battery. The battery 4 should be relatively small and light in order to make disposal easy and safe. The battery 4 should be small enough to be encompassed within the casing. The casing 8 should have a length of at least approximately 80 millimeters and a width of at least approximately 10 millimeters.

Figure 2:
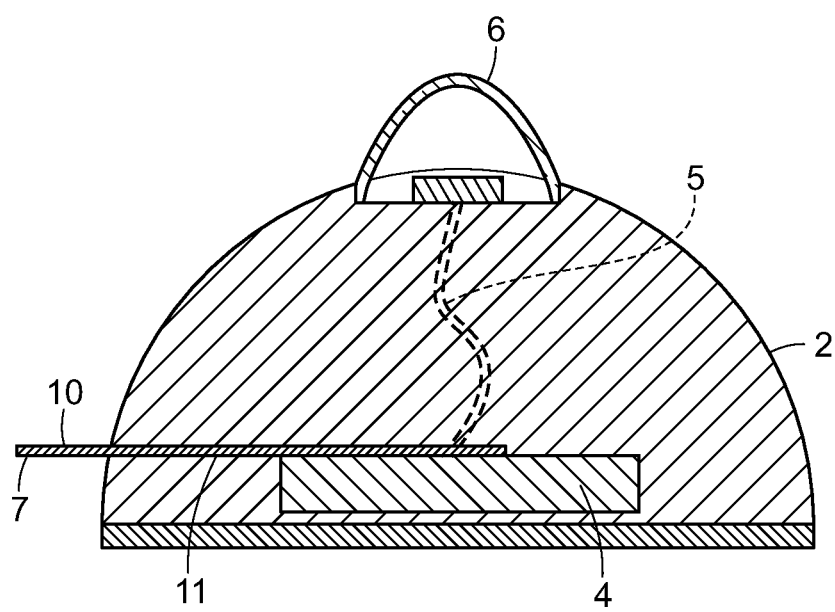
FIG. 2 shows a sectional view of an embodiment of the invention.
Figure 3:
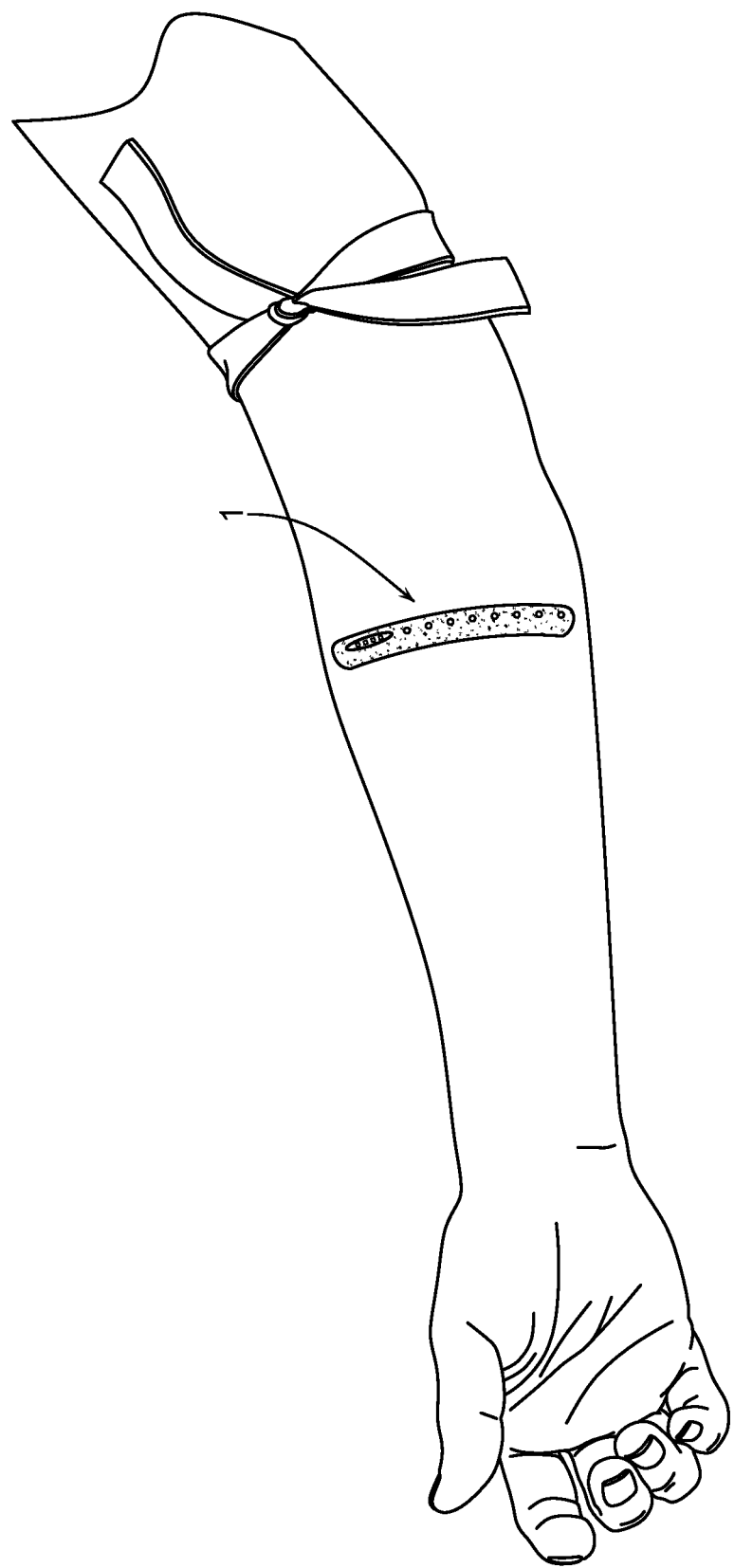
FIG. 3 shows an embodiment of the invention attached to a limb.
Figure 4:
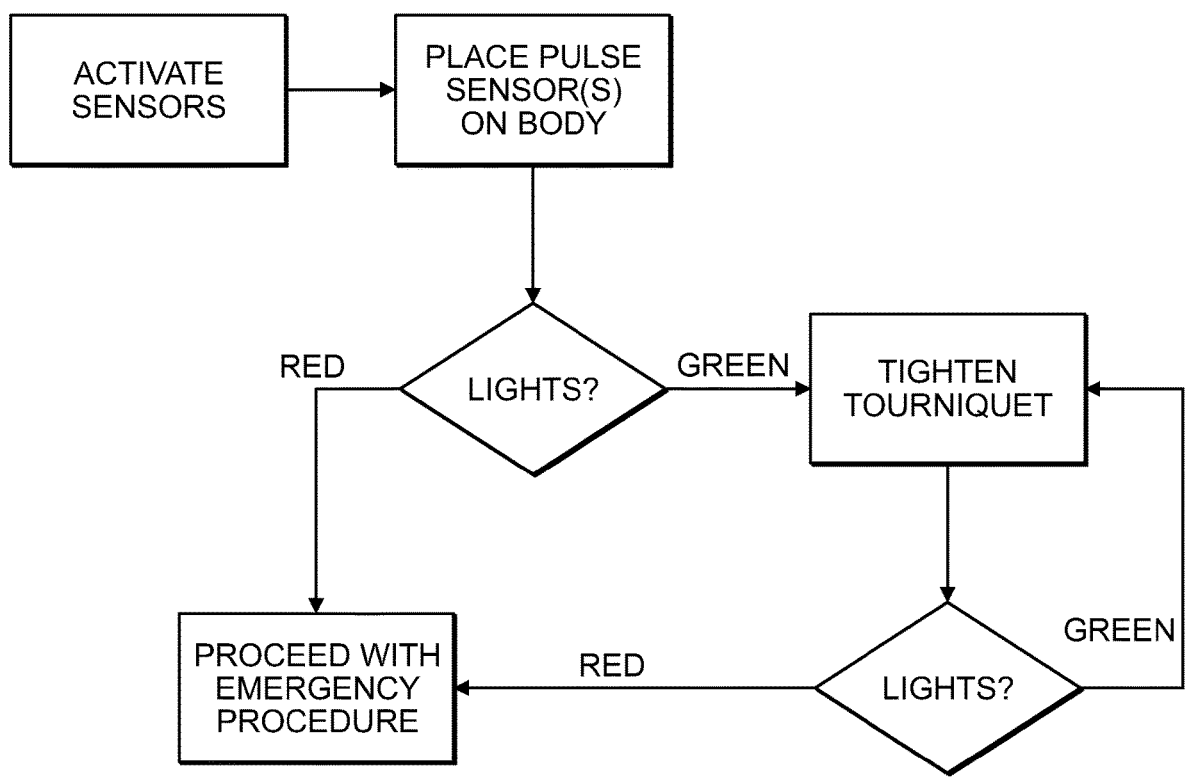
FIG. 4 shows a method for using an embodiment of the invention.

Another aspect of the application, seen in FIG. 2, is the divider 7 that divides the power source 4 or battery from the power connectors. The divider 7 ensures that the battery 4 is not getting drained in storage. The divider 7 can include a first section 11 located inside the casing and a second section 10 located outside the casing. This allows a user to easily access and remove the divider 7 when it's time to use the device. The divider 7 can be pulled out before or after the device 1 is placed on the body. The removal of the divider 7 will activate the device. The divider 7 can be made of plastic, or any other non-conductive material FIG. 4, is a decision tree depicting a method of using a pulse sensing device. Steps include providing a pulse sensing device, as described above, preferably including four sensors, arranged in line, parallel, in an X shape or any other suitable orientation. A user could then place the device on a body part or limb with the adhesive layer contacting the skin and engage the power source. The power source can be engaged using a button or switch or by pulling out a divider as described above. Once an activated device is placed on a body part, the lights will indicate whether a pulse is detected or not. Depending on the application, the lights can be programmed to react in various ways. In a dismemberment situation, or other situation with heavy bleeding, it's important to ensure minimal blood loss. In this example a red or green light can be lit if any of the sensors detect a pulse above 5 beats per minute. If such a pulse is detected, there is still too much arterial flow through that section. If the device is an elongated shape, the lights could be programmed to display where the flow is below a necessary threshold and where it is above said threshold. If the detected flow is above 5 beats per minute or any other threshold, a tourniquet can be applied in order to stop the blood loss. The lights or a change in the light could then signal a change in pulse and arterial flow. If the lights do not change, the tourniquet can be readjusted, or tightened using more force. This step can be repeated until the light source is deactivated or a required light indicator color is reached, signaling that the blood flow is stopped or is low enough.

In alternative use, the device can be placed during on a patient to ensure that a proper amount of pulse is detected and that excessive time is not wasted on giving CPR.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A pulse sensing device comprising:
   a main body comprising at least a pair of sensors, a power source, a power connector, a processor, at least one light source electrically coupled to the at least a pair of sensors, the at least a pair of sensors being configured to detect a pulse, and a divider configured to separate the power source from the power connector,
wherein the processor is configured to detect the pulse and cause the at least one light source to emit at least a first output and a second output,
wherein the first output and the second output correspond to a frequency of the pulse,
wherein the first output corresponds to a first frequency of the pulse, and
wherein the second output corresponds to a second frequency of the pulse;
a casing surrounding the main body; and
an adhesive layer located on a surface of the casing.

2. The pulse sensing device of claim 1, wherein the at least a pair of sensors comprise photo sensors.

3. The pulse sensing device of claim 1, wherein the at least a pair of sensors comprise lasers.

4. The pulse sensing device of claim 1, wherein the at least a pair of sensors comprise oximetry sensors.

5. The pulse sensing device of claim 1, wherein the casing comprises non-latex medical grade disposable foam.

6. The pulse sensing device of claim 1, wherein the casing comprises PVA foam.

7. The pulse sensing device of claim 1, wherein the casing is deformable.

8. The pulse sensing device of claim 1, wherein the at least one light source is a light emitting diode.

9. The pulse sensing device of claim 1, wherein the power source is a non-rechargeable battery.

10. The pulse sensing device of claim 1, wherein the main body has a length of at least 80 millimeters and a width of at least 10 millimeters.

11. The pulse sensing device of claim 1, wherein a ratio of the at least a pair of sensors to a length of the main body is at least 2 sensors to 10 millimeters.

12. The pulse sensing device of claim 1, wherein the ratio of the at least a pair of sensors to the at least one light source is at least 2 to 1.

13. The pulse sensing device of claim 1, wherein the divider comprises a first section located inside the casing and a second section located outside the casing.

14. The pulse sensing device of claim 1, wherein the divider is plastic.

15. A method of using a pulse sensing device, comprising the steps of:
providing a pulse sensing device of claim 1;
contacting an adhesive layer of the pulse sensing device to a body part of a person in need;
applying a tourniquet with a first amount of force at a first location to the person in need;
adjusting, based on an output of at least one light source of the pulse sensing device, at least one property of the tourniquet,
wherein if the output signifies a pulse is detected, then a position of the tourniquet and/or the first amount of force is adjusted, and
wherein if the output signifies no pulse is detected, then a position of the tourniquet remains with the first amount of force at the first location.

16. The method of claim 15, wherein the pulse detected is above 5 beats per minute.

17. The method of claim 15, wherein the pulse detected is at least 25% of a normal sinus rhythm.

18. The method of claim 15, further comprising the step of: the light source being deactivated.

19. The method of claim 15, wherein to engage the power source the user removes the divider.

20. The pulse sensing device of claim 1, wherein the first frequency of the pulse is at or above 30 beats per minute and the second frequency of the pulse is below 30 beats per minute.

* * * * *